(12) United States Patent
Shih et al.

(10) Patent No.: US 7,335,345 B2
(45) Date of Patent: Feb. 26, 2008

(54) SYNTHESIS OF WATER SOLUBLE NANOCRYSTALLINE QUANTUM DOTS AND USES THEREOF

(75) Inventors: Wei-Heng Shih, Bryn Mawr, PA (US); Wan Y. Shih, Bryn Mawr, PA (US); Hui Li, Philadelphia, PA (US); Melissa Colleen Schillo, Broadview Heights, OH (US)

(73) Assignee: Drexel University, Philadelphia, PA (US)

( * ) Notice: Subject to any disclaimer, the term of this patent is extended or adjusted under 35 U.S.C. 154(b) by 303 days.

(21) Appl. No.: 11/136,653

(22) Filed: May 24, 2005

(65) Prior Publication Data

US 2006/0078490 A1    Apr. 13, 2006

Related U.S. Application Data

(60) Provisional application No. 60/573,804, filed on May 24, 2004.

(51) Int. Cl.
*H01M 9/08* (2006.01)
(52) U.S. Cl. .................. 423/561.1; 423/566.1; 977/774; 252/301.4 R; 252/301.6 R; 252/301.6 S; 252/301.4 S; 252/301.4 F
(58) Field of Classification Search ............. 423/561.1, 423/566.1; 977/774; 252/301.4 R, 301.6 R, 252/301.6 S, 301.4 S, 301.4 F
See application file for complete search history.

(56) References Cited

U.S. PATENT DOCUMENTS

| | | | |
|---|---|---|---|
| 4,751,200 | A | 6/1988 | Gmitter et al. |
| 5,747,180 | A * | 5/1998 | Miller et al. ................. 428/601 |
| 5,985,353 | A | 11/1999 | Lawton et al. |
| 6,251,303 | B1 | 6/2001 | Bawendi et al. |
| 6,333,110 | B1 | 12/2001 | Barbera-Guillem |
| 6,350,515 | B1 | 2/2002 | Lawton et al. |
| 6,426,513 | B1 | 7/2002 | Bawendi et al. |
| 6,444,143 | B2 | 9/2002 | Bawendi et al. |
| 6,468,808 | B1 | 10/2002 | Nie et al. |
| 6,576,291 | B2 | 6/2003 | Bawendi et al. |
| 6,623,559 | B2 | 9/2003 | Huang |
| 7,151,047 | B2 * | 12/2006 | Chan et al. ................. 438/497 |
| 7,214,428 | B2 * | 5/2007 | Naasani ....................... 428/403 |
| 2007/0042576 | A1 * | 2/2007 | Chan et al. ................. 438/497 |

OTHER PUBLICATIONS

Mark L. Brongersma, *Nanoshells: gifts in a gold wrapper*, Nature Materials, vol. 2, May 2003.

Sharron G. Penn, Lin He and Michael J. Natan, *Nanoparticles for bioanalysis*, Current Opinion in Chemical Biology 2003, 7:609-615.

Sabrina Foglia, Lorenza Suber, Marcofabio Righini, *Size tailoring of CdS nanoparticles by different colloidal chemical techniques*, Colloids and Surfaces, A: Physicochemical and Engineering Aspects 177 (2001) 3-12.

Caroline Seydel, *Quantum Dots Get Wet*, Science, vol. 300, Apr. 4, 2003, pp. 80-81.

B.O. Dabbousi, J. Rodriguez-Viejo, F.V. Mikulec, J.R. Heine, H. Mattoussi, R. Ober, K.F. Jensen and M.G. Bawendi, *(CdSe)ZnS Core—Shell Quantum Dots: Sythesis and Characterization of a Size Series of Highly Luminescent Nanocrystallites*, J. phys. Chem. B, 1997, 101, 9463-9475.

Marcel Bruchez Jr., Mario Moronne, Peter Gin, Shimon Weiss, A. Paul Alivisatos, *Semiconductor Nanocrystals as Fluorescent Biological Labels*, Science, vol. 281, Sep. 25, 1998, 2013-2016.

Daniele Gerion, Fabien Pinaud, Shara C. Williams, Wolfgang J. Parak, Daniela Zanchet, Shimon Weiss and Paul Alivisatos, *Synthesis and Properties of Biocompatible Water-Soluble Silica-Coated CdSe/ZnS Semiconductor Quantum Dots*, J. Phys Chem B, 2001, 105, 8861-8871.

Mark Green, Robin Taylor and Gareth Wakefield, *The synthesis of luminescent adenosine triphosphate passivated cadmium sulfide nanoparticles*, J. Mater. Chem, 2003, 13, 1859-1861.

A.L. Rogach, L. Katsikas, A. Kornowski, Dangsheng Su, A. Eychmüller and H. Weller, *Synthesis and Characterization of Thiol-Stabilized CdTe Nanocrystals*, Ber. Bunsenges. Phys. Chem. 100, 1772-1778 (1996) No. 11.

B.V. Enüstün and John Turkevich, *Coagulation of Colloidal Gold*, Journal of the American Chemical Society, vol. 85, No. 21, Nov. 5, 1963, 3317-3328.

M.K. Chow and C. F. Zukoski, *Gold Sol Formation Mechanisms: Role of Colloidal Stability*, Journal of Colloid and Interface Science, 165, 97-109 (1994).

(Continued)

*Primary Examiner*—Timothy C. Vanoy
(74) *Attorney, Agent, or Firm*—Knoble Yoshida & Dunleavy, LLC

(57) ABSTRACT

An economic, direct synthetic method for producing water soluble QDs that are ready for bioconjugation is provided. The method can produce aqueous QDs with emission wavelengths varying from 400 nm to 700 nm. Highly luminescent metal sulfide (MS) QDs are produced via an aqueous synthesis route. MS QDs are capped with thiol-containing charged molecules in a single step. The resultant MS QDs exhibit the distinctive excitonic photoluminescence desired of QDs and can be fabricated to avoid undesirable broadband emissions at higher wavelengths. This provides a significant improvement over the present complex and expensive commercial processes for the production of QDs. The aqueous QDs are stable in biological fluids over a long period of time. In addition, nontoxic ZnS QDs have been produced with good photoluminescence properties by refluxing the ZnS QD suspensions over a period of time.

15 Claims, 2 Drawing Sheets

OTHER PUBLICATIONS

Zhan Li, Yumin Du, *Biomimic synthesis of CdS nanoparticles with enhanced luminescence*, Science Direct, Materials Letters 57 (2003) 2480-2484.

Richard Kho, Claudia L. Torres-Martinez and Rajesh K. Mehra, *A Simple Colloidal Synthesis for Gram-Quantity Production of Water-Soluble ZnS Nanocrystal Powders*, Journal of Colloid and Interface Science 277, 561-566 (2000).

Warren CW Chan, Dustin J. Maxwell, Xiaohu Gao, Robert E. Bailey, Mingyong Han and Shuming Nie, *Luminescent quantum dots for multiplexed biological detection and imaging*, Current Opinion in Biotechnology 2002, 13:40-46.

L.E. Brus, *Electron-electron and electron-hole interactions in small semiconductor crystallites: The size of dependence of the lowest excited electronic state*, J.Chem.Phys. 80(9), May 1, 1984, 4403-4409.

Darren Lawless, Sudhir Kapoor and Dan Meisel, *Bifunctional Capping of CdS Nanoparticles and Bridging to TiO2*, J. Phys. Chem. 1995, 99, 103259-10335.

\* cited by examiner

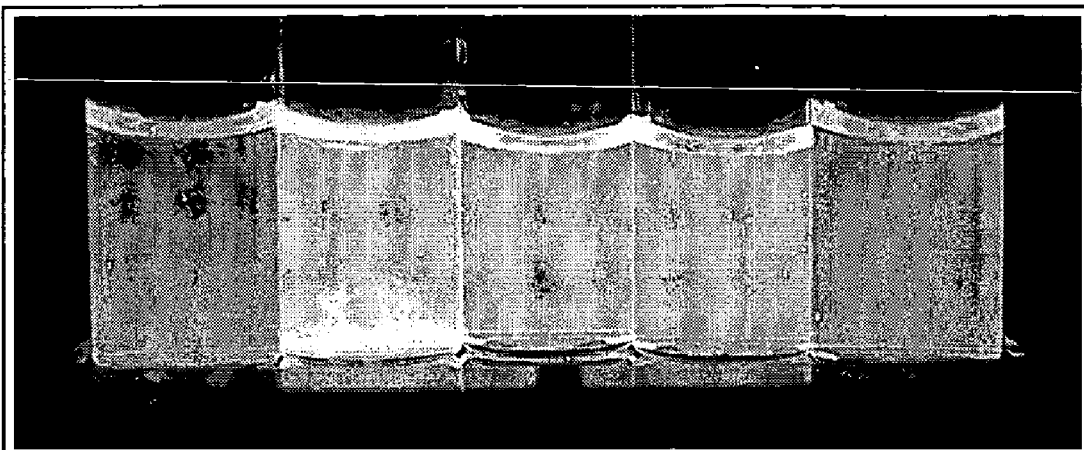
Fig.1. Five distinct emission colors of CdS and ZnS-doped CdS QDs excited with a UV lamp. From left to right (red to blue), the emission maxima are located at 660, 620, 550, 515 and 475 nm.
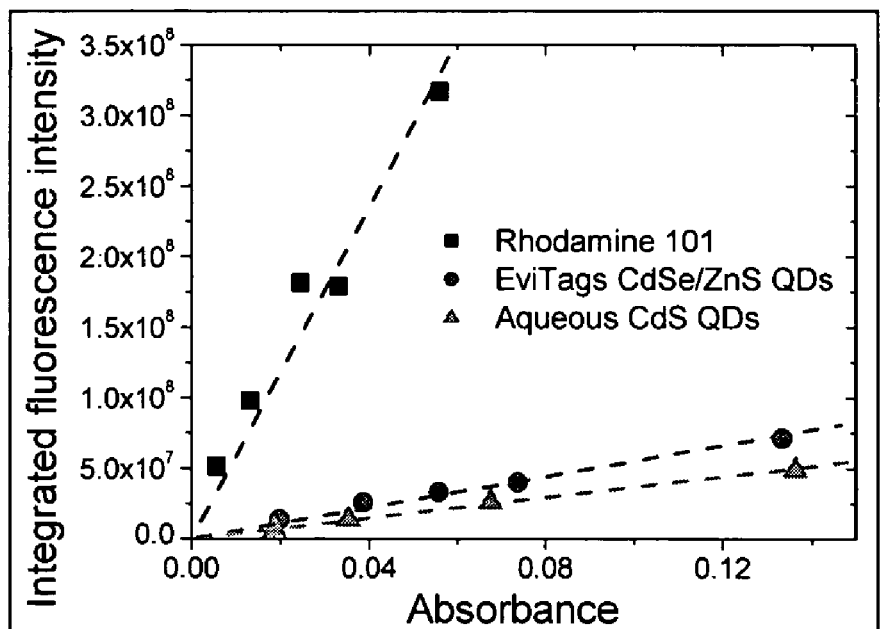
Fig. 2. Integrated photoluminescence intensity vs. absorbance for Rhodamine 101, EviTags™ CdSe/ZnS QDs and aqueous CdS QDs.

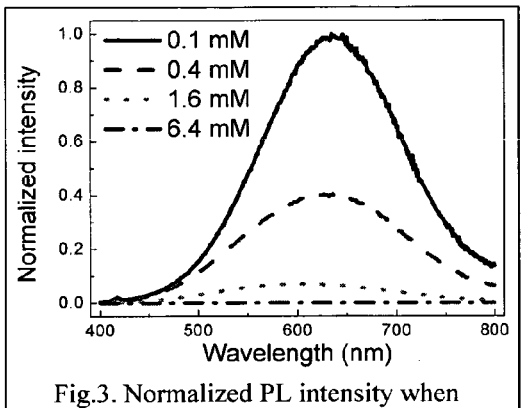

Fig.3. Normalized PL intensity when excited by a UV light of wavelength 365 nm. The intensity is normalized by the concentration and the peak PL of the lowest concentration is set to be 1.

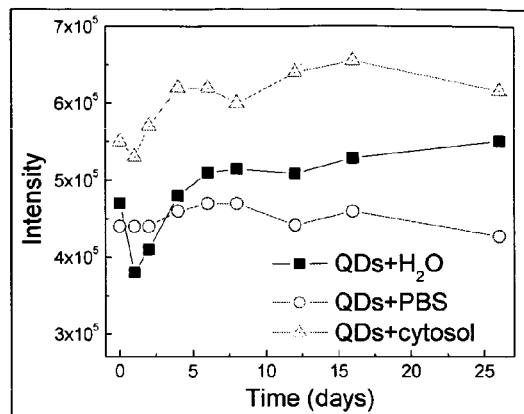

Fig.4. The PL intensity of aqueous CdS QDs as a function of time in water, PBS, and cytosol, respectively.

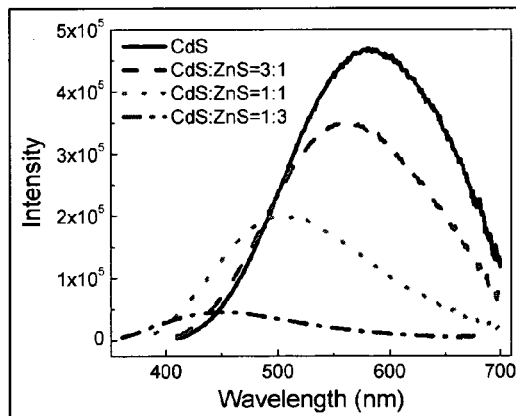

Fig.5. The PL intensity of aqueous CdS QDs with different amount of ZnS doping. As Zn content increases, the peak shifts to lower wavelength.

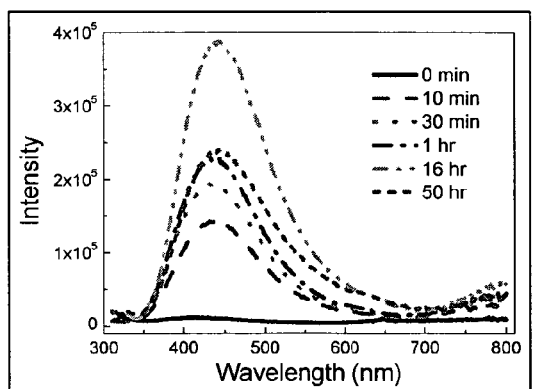

Fig.6. PL intensity of ZnS after reflux at different amount of time. Reflux at 100°C for 16 hrs gives the highest intensity.

SYNTHESIS OF WATER SOLUBLE NANOCRYSTALLINE QUANTUM DOTS AND USES THEREOF

CROSS-REFERENCE TO RELATED APPLICATIONS

This application claims the benefit of U.S. provisional patent application no. 60/573,804, filed on May 24, 2004, pursuant to 35 U.S.C. § 119(e).

1. STATEMENT OF GOVERNMENT INTEREST

This invention was reduced to practice with Government support under RO1 EB00720-01 awarded by NIH; the Government is therefore entitled to certain rights to this invention.

BACKGROUND OF THE INVENTION

2. Field of Invention

The present invention relates to the aqueous synthesis of photoluminescent nanocrystalline quantum dots.

3. Brief Description of the Prior Art

Semiconductor nanocrystalline quantum dots (QDs) with bioconjugates on the surface have been studied extensively because of their unique optical properties. QDs are inorganic nanoparticles that emit light at a specific wavelength when excited by light. When light shines on QDs, electrons in the valence band are excited to the conduction band, forming short-lived (nanoseconds) electron-hole pairs called excitons, which emit photons of a specific wavelength when the electron-hole pairs eventually recombine. The excitonic emission is independent of the wavelength of the excitation light. This makes it easier to excite QDs to luminescence than the traditional fluorescent molecules that require a specific excitation wavelength. The wavelength of the emitted photons of QDs, on the other hand, is specific and can be controlled by the QDs' particle size and composition. The synthesis of QDs was developed mostly in the 1990's. In the last few years, the interest in using QDs in biomedical imaging has exploded due to advances in surface modification of QDs that have made them accessible for antibody immobilization and detection of antibody-antigen binding.

Using QDs as imaging markers inside living organisms is one of the exciting new nanobiotechnologies. QDs can be used as biological markers to find a disease as well as to carry a drug to the exact cell that needs it by immobilizing antibodies on the surface of the QDs. QDs may be specific to a particular disease and may be tailored to bind only to infected cells. Detection may be carried out either by locating the QDs' particles or by detecting signals emanating from the QDs' particles. For example, luminescence of antibody-coated QDs bound to the cancerous tissue in a mouse helped locate the tumor.[1] Until now the main biological tags that have been employed are organic fluorophores or radioactive labels.[2] Radioactive labels are short lived and radioactive. Concerns about the use of radioactive materials in the body always arise. Organic fluorophores have wide emission spectra and the emission is not as bright as that of QDs. In comparison to conventional dye molecules, QDs have the advantages of having tunable fluorescence signatures, narrow emission spectra, brighter emissions, and good photostability.[3] Due to the enormous interest in using QDs as biological tags, QDs are now commercially available from quite a number of companies. However, the complexity of the existing organic-based synthesis route for fabricating commercial QDs makes the price prohibitively high, as much as U.S. $1200/g without bio-conjugation[4], and $3200/mg for bioconjugated QDs.[5] Part of the complexity of the existing QDs production technology stems from the need to improve the photoluminescence yield by eliminating the broadband emission of earlier QDs by capping with an inorganic layer. Making QDs water-soluble is another challenge for biomedical applications.

Both groups II-VI nanocrystals such as CdSe, CdTe, CdS,[6,7] ZnS,[8] and ZnSe, and groups III-V nanocrystals such as InP and InAs have been synthesized and studied extensively in the past.[9] One type of quantum dot currently on the market is based on CdSe nanocrystals capped by, for example, ZnS. The synthesis follows the method popularized by Bawendi's group at MIT involving the pyrolysis of organometallic precursors, dimethylcadmium and trioctylphosphine oxide (TOPO) to form CdSe nanocrystals. ZnS capping on CdSe was done using diethylzinc and hexamethyldisilathiane precursors.[10]

Alivisatos and coworkers further made QDs water-soluble by addition of a silica/siloxane coating.[11] With a silica coating, 3-(mercaptopropyl) trimethoxysilane (MPS) is then adsorbed on the nanocrystals and displaces the TOPO molecules, making the surface of the QDs suitable for antibody immobilization.[12] These processes are complex involving multiple steps and a change of solvent from organic to aqueous during the process.

An aqueous process for the manufacture of CdS QDs was published recently using adenosine triphosphate (ATP) as the capping molecule.[13] This process suffers from the disadvantage that the luminescence spectrum of the resultant CdS QDs includes an undesirable non-excitonic broadband emission between 500 nm to 700 nm wavelength.

Rogach et al.[14] describes the synthesis of oxidation-stable CdTe nanoclusters in aqueous solution using 2-mercaptoethanol and 1-thioglycerol as stabilizers. CdTe nanocrystals generally have no luminescent properties until they are stabilized with 2-mercaptoethanol. However, this capping method also yields QDs with an undesirable broadband emission at higher wavelengths. Similarly, when CdTe was stabilized with thioglycerol, a broadband emission at higher wavelengths was also observed. Currently, only the capping of inorganic materials, for example, a ZnSe shell on CdTe core, can eliminate the undesirable broadband emission. Thus, there remains a need for an economic, direct aqueous synthesis route for the production of highly luminescent water-soluble nanocrystalline QDs.

SUMMARY OF THE INVENTION

In one aspect, the present invention relates to a process for the production of QDs in aqueous media, which are ready for bioconjugation. In the process, water-soluble precursors are employed to manufacture QDs in an economic and environmentally-friendly process in aqueous media. The process involves the reaction of a water-soluble salt of a metal suitable for use in QDs with a thiol-functionalized molecule and a water-soluble sulfide. The resultant products are ready for bioconjugation and may exhibit improved emission spectra, relative to other QDs fabricated in aqueous media.

BRIEF DESCRIPTION OF THE DRAWINGS

FIG. 1 shows emissions of CdS and ZnS-doped CdS QDs excited with a UV lamp. From left to right (red to blue), the emission maxima are located at 660, 620, 550, 515 and 475 nm.

FIG. 2 shows integrated photoluminescence intensity vs. absorbance for Rhodamine 101, EviTags™ CdSe/ZnS QDs and aqueous CdS QDs.

FIG. 3 shows normalized PL intensity when excited by UV light of a wavelength of 365 nm. The intensity is normalized by the concentration and the peak PL of the lowest concentration is set to be 1.

FIG. 4 shows the PL intensity of aqueous CdS QDs as a function of time in water, PBS, and cytosol, respectively.

FIG. 5 shows the PL intensity of aqueous CdS QDs with different amount of ZnS doping. As Zn content increases, the peak shifts to a lower wavelength.

FIG. 6 shows the PL intensity of ZnS after reflux for different time periods. Reflux at 100° C. for 16 hrs gave the highest intensity in this example.

DETAILED DESCRIPTION OF THE PREFERRED EMBODIMENTS

In a first aspect, the present invention relates to an economic, direct synthetic method for producing water soluble QDs that are ready for bioconjugation. Highly luminescent metal sulfide (MS) QDs are produced via an aqueous synthesis route. The resultant MS QDs may then be capped with carboxylated molecules in a single step. The capped MS QDs generally exhibit the distinctive excitonic photoluminescence desired of QDs without the undesirable broadband emission at higher wavelengths often present in other QDs fabricated in aqueous media, indicating that the aqueous process of the present invention is effective in producing the substantially clean MS surface that appears to be necessary for a high luminescence yield. This is significant because, as far as the inventors are aware, no known aqueous method has completely eliminated the tendency for the QDs to exhibit an undesirable broadband emission at higher wavelengths.

Furthermore, the carboxylated molecules used to cap the particle surface of the MS QDs render the MS QDs ready for surface immobilization of antibodies and other biomolecules. That the surface of the MS QDs is immediately ready for further biological modification in a single step also represents a significant advantage over the manufacture of QDs by other methods. This results in substantially reduced material costs. In addition to the economic benefits and the potential impact on fundamental research in the field of surface chemistry, the aqueous processing route of the present invention is environmentally friendly and readily adapted to commercial production levels.

In general, the manufacturing process of the present invention may be applied to fabricate QDs from water-soluble precursors. Thus, any QDs that can be made from water-soluble precursors are within the scope of the present invention.

In the manufacturing process of the present invention, any salt of a metal suitable for use in a quantum dot, that is soluble in water, may be employed as a starting-material. Exemplary water-soluble metal salts that may be employed in the invention are metals that can form sulfides, such as $Cd(NO_3)_2$, $Cd(ClO_4)_2$, $CdCl_2$, $CdSO_4$, cadmium acetate, $Zn(NO_3)_2$, $Zn(ClO_4)_2$, $ZnSO_4$, $ZnCl_2$, zinc acetate, $Mn(NO_3)_2$, $Mn(ClO_4)_2$, $MnSO_4$, $MnCl_2$, manganese acetate, $Pb(NO_3)_2$, $Pb(ClO_4)_2$, $PbSO_4$, $PbCl_2$, and lead acetate.

Any suitable water-soluble sulfide may be used as a reactant in the process of the invention. Exemplary water-soluble sulfides that may be employed in the invention include $Na_2S$, and exemplary metal sulfides that may be employed in the present invention include CdS, ZnS and PbS. Also, sulfide gases, such as $H_2S$, may be bubbled through the aqueous solution in the process of the invention. The addition of sulfide is preferably done gradually, such as by titration, with stirring, and may take, for example, about 2 hours. Generally, it is desirable to use about a stoichiometric amount of the sulfide. However, varying the amount of sulfide from a stoichiometric amount can, in some cases, produce desirable variations in the particle sizes of the particles in the QDs and thus, it may be useful to use anywhere from 0.1 to 10 times the stoichiometric amount of sulfide, more preferably 0.5 to 5 times the stoichiometric amount of the sulfide, and most preferably about 0.8-1.2 times the stoichiometric amount of the sulfide. The stoichiometric amount is based on the reaction of the sulfide with the metal to form the metal sulfide.

Also, any thiol-functionalized molecule with a charged group, preferably on the opposite end, may be used as a reactant in the process of the invention, as long as the thiol-functionalized molecule is water-soluble. Exemplary thiol-functionalized molecules for use in the present invention include 4-aminothiophenol, mercaptosilanes such as 3-mercaptopropyltrimethoxysilane, and similar materials, as well as mercaptocarboxylic acids such as mercaptoacetic acid, mercaptopropionic acid, mercaptosuccinic acid, mercaptobenzoic acid, and mercaptoundecanoic acid. Any concentration of thiol-functionalized molecule may be employed, as long as it is within the solubility limit of the thiol-functionalized molecule in aqueous media.

The ratio of the various reactants is not critical and, in fact, may be varied in order to customize the particle size of the resultant capped QDs. In generally, however, the molar ratio of thiol groups to metal may vary from about 1 to about 100, though ratios of 1-5 are more preferred, with a ratio of about 2 being most preferred.

In one embodiment of the invention, highly luminescent CdS QDs that are capped with mercaptocarboxylic acids (MCA) in a single step, are synthesized. Fluorescence results indicate that the CdS QDs exhibit bright fluorescence in the visible range from blue to red as exemplified in FIG. 1. In FIG. 1, the emissions of CdS QDs synthesized by the method of the present invention are shown. These emissions exhibit different fluorescent colors when excited by a 365 nm UV lamp. Any water-soluble Cd salt may be used, including but not limited to, cadmium nitrate, cadmium acetate, cadmium chloride, cadmium hydroxide, and cadmium sulfate. The molar ratios between the MCA and Cd may vary from about 1 to about 100. More preferably, the molar ratio between the MCA and the Cd is from about 1.5 to about 3, and most preferably about 2.

One advantage of certain embodiments of the present invention is the elimination of the broadband emission of the resultant QDs. A second advantage of certain embodiments of the invention is that a one-step, aqueous process produces QDs capped with $COO^-$, which can readily be activated to form a peptide bond with an amine group of a protein, i.e., is ready for antibody/receptor immobilization on the QD surface. A typical reaction time for the step of chelating Cd with MCA is about 12 hours, though the reaction time may vary depending on the specific reactants and reaction conditions employed. It will be understood by those of ordinary skill in the art that reaction times and conversion rates are not critical to the process of the present invention.

In a more preferred aspect, CdS QDs are synthesized using 3-mercaptopropionic acid ($HSCH_2CH_2COOH$) (MPA), cadmium nitrate ($Cd(NO_3)_2$) and sodium sulfide ($Na_2S$). For biological applications, such as biomarkers, where antibodies need to be conjugated to the QDs, aqueous suspensions of QDs are most desirable since the conjugation process can be accomplished directly in the aqueous suspension without further preparative steps. However, precipitates may be produced for shipping or other reasons. Such precipitates can be reconstituted before use, if desirable.

In another aspect, a capping molecule capable of chelating with Cd ions to minimize the formation of impurity states due to dangling Cd ions is required. These capping molecules should as act to stabilize and limit the growth of the particles. 3-mercaptopropionic acid ($HSCH_2CH_2COOH$) (MPA) is preferred as the capping molecule because it has a thiol group that can bind to Cd. This follows the example of synthesizing monodispersed gold suspensions using sodium citrate.[15] Citrate not only reduces the gold but also serves as the capping molecule to stabilize the gold particles. By varying the ratio of citrate to gold, gold particle size is controlled.[16] Without being bound by theory, MPA may play a similar role to cap and stabilize CdS particles in the QDs.

Occasionally, difficulties may arise during the reaction if the pH of the reaction mixture is in the vicinity of the isoelectric point (IEP) of the metal sulfide. Thus, in such cases, it may be desirable to adjust the pH of the reaction mixture away from the JEP using a suitable, water-soluble pH-adjusting agent, before the addition of sodium sulfide. One example of a suitable pH-adjusting agent is ammonium hydroxide. The concentration of the pH-adjusting agent may be varied, as necessary, to produce optimum results. Preferred concentrations of ammonium hydroxide are in the range of about 0.5-2M and, more preferably, about 0.8-1.2 M, with about 1M being the most preferred concentration of the ammonium hydroxide pH-adjusting agent.

After adjustment of the pH away from the IEP of the metal sulfide, sodium sulfide is added quickly to minimize the reaction time. A few minutes of reaction time is sufficient. The process is best performed in oxygen-free environment to avoid the photo-oxidation reaction of sulfur. To prevent particle growth, the reacted solution is quenched to freezing point of water and then stored in refrigerator.

EXAMPLE I

Aqueous Synthesis of CdS QDs $1.6 \times 10^{-4}$ mol $Cd(NO_3)_2$, $1.6 \times 10^{-4}$ mol $Na_2S$, and $3.2 \times 10^{-4}$ mol MPA, respectively, were prepared and each was dissolved into about 33 ml deionized water with stirring. The $Cd(NO_3)_2$ solution was added to the MPA solution at 2 ml/min with continuous stirring. $NH_4OH$ (1 M) was added to the mixed solution to adjust the pH value to a pH of about 7-9. The $Na_2S$ solution was then quickly poured into the mixed solution and stirred for about 3-5 min. All of the above process steps were performed in an oxygen-free environment. In the present example, these steps were performed in a sealed glove bag pumped with nitrogen flow. An ultrasonicator was used to apply sonication for about 5-10 min. Large agglomerates were removed by filtration, as necessary. CdS nanoparticles were obtained in a clear suspension. The suspension was quenched in a freezer to 0° C., and the suspension was stored in a refrigerator at about 4° C.

EXAMPLE II

Aqueous Synthesis of ZnS QDs

The procedure was the same as in the example I, except that the chemical precursor $Cd(NO_3)_2$ was replaced by $Zn(NO_3)_2$. After the ZnS QDs were prepared, the suspension was refluxed at 100° C. for several hours to help improve the photoluminescence properties.

EXAMPLE III

Aqueous Synthesis of CdS QDs with ZnS Doping $0.8 \times 10^{-4}$ mol $Cd(NO_3)_2$ and $0.8 \times 10^{-4}$ mol $Zn(NO_3)_2$, respectively, were prepared and each dissolved into 16 ml deionized water with stirring. $1.6 \times 10^{-4}$ mol $Na_2S$ and $3.2 \times 10^{-4}$ mol MPA, respectively, were weighed and each dissolved into 33 ml deionized water with stirring. The $Cd(NO_3)_2$ solution was added into the MPA solution and then the $Zn(NO_3)_2$ solution was added into MPA solution at about 2 ml/min with continuous stirring. Thereafter, the process described in Example I was followed. The CdS with ZnS doping (1:1) QDs are obtained as a clear suspension. Other doping ratios can be employed by adjusting the Cd to Zn molar ratio.

Quantum Yield

To obtain the quantum yield of the aqueous CdS QDs, Rhodamine 101 was used as the standard sample, and the commercial QDs were compared. All the measurements were performed at the same conditions for Rhodamine 101, for the commercial EviTags™ CdSe/ZnS QDs and for the aqueous CdS QDs of the present invention. For each sample, the absorbance and integrated photoluminescence (PL) intensity were collected at a fixed excitation wavelength 365 nm for several different concentrations. The absorbance was always kept below 0.15 to eliminate the re-absorption interaction effect. Using Rhodamine 101 dissolved in ethanol as the standard sample with known quantum yield of 100%, the quantum yield of EviTags™ CdSe/ZnS QDs was found to 8.9%, and the quantum yield of the aqueous CdS QDs was 6.0%. Without the core-shell structure, the aqueous CdS QDs have achieved high quantum yield comparable to that of the commercially available EviTags™. FIG. 2 shows integrated photoluminescence intensity vs. absorbance for Rhodamine 101, EviTags™ CdSe/ZnS QDs and aqueous CdS QDs.

Concentration Effect

It was found that the PL properties of the aqueous QDs depend on the precursor concentration. For the samples synthesized at different Cd precursor concentrations of from 0.1 mM to 6.4 mM, the emission spectra varied. There was no linear relationship between the PL intensity of CdS QDs and the precursor concentration. FIG. 3 shows the normalized PL intensity of aqueous QDs for several precursor concentrations. After normalization based on the concentration, the QDs with the lowest precursor concentration displayed the highest PL intensity. It is speculated that at high precursor concentration, not all precursor was nucleated and grown into particles. Perhaps the excess precursors remained in the solution and didn't contribute to the PL intensity.

Stability

The CdS QDs suspension obtained using a precursor concentration of 1.6 mM was mixed at a volume ratio of 1:3 with de-ionized water, phosphate buffer solution (PBS (1×)) and cytosol ($10^6$ cells/ml), respectively. FIG. 4 shows the PL intensity of aqueous QDs in the three solutions for up to 26 days, during which the samples were stored in the refrigerator at 4° C. away from normal daylight. The samples were taken out of the refrigerator for PL measurements on the designated days. It was shown that the aqueous CdS QDs have good stability with de-ionized water, PBS and cytosol. The results indicate that the aqueous QDs can be used as excellent fluorescence markers in biological solutions for biomedical imaging over a long period of time due to their stability.

Effects of ZnS Doping

ZnS was added to the CdS QDs to create different wavelengths of photoluminescence. FIG. 5 shows the PL intensity of ZnS-doped CdS QDs at several different ZnS contents. As the concentration of ZnS increases, the PL peak shifts toward smaller wavelengths. However, the PL intensity also decreases with increasing amount of ZnS.

ZnS: Effect of Reflux

Pure ZnS QDs were synthesized as a candidate for nontoxic quantum dots. Zn is not harmful to the human body and thus ZnS would be suitable for an in vivo study. Refluxing the ZnS QD suspensions can increase the PL intensity as shown in FIG. 6. Refluxing for too long is detrimental resulting in agglomerated QDs. For 1.6 mM ZnS QDs, refluxing for 16 hrs gave the best intensity.

Another alternative is to employ hydrothermal refluxing at high temperatures.

It is to be understood, however, that even though numerous characteristics and advantages of the present invention have been set forth in the foregoing description, together with details of the structure and function of the invention, the disclosure is illustrative only, and changes may be made in detail, especially in matters of shape, size and arrangement of parts within the principles of the invention to the full extent indicated by the broad general meaning of the terms in which the appended claims are expressed.

REFERENCES, DISCLOSURES OF WHICH ARE HEREBY INCORPORATED BY REFERENCE IN THEIR ENTIRETY

[1] Quantum Dots Get Wet, *Science*, volume 300, p.80, Apr. 4, 2003.
[2] S. G. Penn, L. He, and M. J. Natan, "Nanoparticles for Bioanalysis", *Curr. Opin. Chem. Bio.*, 7, 1-7, (2003)
[3] M. L. Brongersma, "Nanoshells, "Gifts in a Gold Wrapper", *Nature Materials*, vol. 2, May 2003.
[4] Applied Nanoworks. http://www.appliednanoworks.com/
[5] Evident Technologies. http://www.evidenttech.com.
[6] S. Foglia, L. Suber, and M. Righini, "Size Tailoring of CdS Nanoparticles by Different Colloidal Chemical Techniques", *Colloid & Surfaces*, 177, 3-12, (2000)
[7] Z. Li and Y. Du, "Biomimic Synthesis of CdS Nanoparticles with Enhances Luminescence", *Mater. Lett.*, 57, 2480-2484, (2003)
[8] R. Ko, C. L. Torres-Martinez, and R. K. Mehra, "A Simple Colloidal Synthesis for Gram-Quantity Production of Water-Soluble ZnS Nanocrystal Powders", *J. Colloid and Interf. Sci.*, 227, 561-566, (2000)
[9] W. C. W. Chan, D. J. Maxwell, X. Gao, R. E Bailey, M. Han, and S. Nie, "Luminescent Quantum Dots for Multiplexed Biological Detection and Imaging," *Curr. Opin. Biotech.*, 13, 40-46 (2002)
[10] B. 0. Dabbousi, J. Rodriguez-Viejo, F. V. Mikulec, J. R. Heine, H. Mattoussi, R. Ober, K. F. Jensen, and M. G. Bawendi, "(CdSe)ZnS Core-Shell Quantum Dots: Synthesis and Characterization of a Size Series of Highly Luminescent Nanocrystallites," *J. Phys. Chem. B,* 101, 9463-9475 (1997)
[11] M. Bruchez, M. Moronne, P. Gin, S. Weiss, and A. P. Alivisatos, "Semiconductor Nanocrystals as Fluorescent Biological Labels," *Science* 281, 2013-2015 (1998)
[12] D. Gerion, F. Pinaud, S. C. Willimas, W. J. Parak, D. Zanchet, S. Weiss, and A. P. Alivisatos, "Synthesis and Properties of Biocompatible Water-Soluble Silica-Coated CdSe/ZnS Semiconductor Quantum Dots," *J Phys Chem B*, 105, 8861-8871 (2001)
[13] M. Green, R. Taylor, and G. Wakefield, "The Synthesis of Luminescent Adenosine Triphosphate Passivated Cadmium Sulfide Nanoparticles," *J. Mater. Chem.*, 13, 1859-1861 (2003)
[14] A. L. Rogash, L. Katsikas, A. Kornowski, Dangsheng Su, A. Eycmuller, and H. Weller, Synthesis and Characterization of Thiol-Stabilized CdTe Nanocrystals", *Ber. Bunsenges. Phys. Chem.*, 100, 1772-1778 (1978)
[15] B. V. Enustun and J. Turkevich, "Coagulation of Colloidal Gold", *J. Am. Chem. Soc.*, 85, (21), 3317-3328, (1963)
[16] M. K. Chow and C. F. Zukoski, "Gold Sol Formation Mechanisms: Role of Colloidal Stability", *J. Colloid & Interf. Sci.*, 165, 97-109, (1994)
[16] L. E. Brus, *J. Chem. Phys.*, 80, 4403 (1984)

What is claimed is:

1. A method for making quantum dots suitable for bioconjugation, said method comprising the steps of:
   a. providing an aqueous solution of at least one metal salt, and at least one thiol-containing charged molecule;
   b. if required, adjusting the pH of the aqueous solution of water-soluble metal salt and thiol-containing charged molecule away from the isoelectric point of a resulting metal sulfide;
   c. adding a water-soluble sulfide to the aqueous solution of at least one metal salt, and at least one thiol-containing charged molecule to precipitate metal sulfide and form quantum dots; and
   d. quenching to about a freezing point of water to form a suspension of quantum dots.

2. A method as claimed in claim 1, further comprising the step of:
   e. refluxing the quenched suspension for a period of time sufficient to improve the emission intensity of the quantum dots.

3. A method as claimed in claim 1, wherein the at least one thiol-containing charged molecule is selected from the group consisting of: mercaptosilanes, mercaptocarboxylic acids, and aminothiols.

4. A method as claimed in claim 3, wherein the at least one thiol-containing charged molecule is selected from the group consisting of: 4-aminothiophenol, 3-mercaptopropyltrimethoxysilane, mercaptoacetic acid, mercaptopropionic acid, mercaptosuccinic acid, mercaptobenzoic acid, and mercaptoundecanoic acid.

5. A method as claimed in claim 1, wherein the metal sulfide is selected from the group consisting of CdS, ZnS, PbS and MnS.

6. A method as claimed in claim 4, wherein the metal sulfide is ZnS.

7. A method as claimed in claim 2, wherein the refluxing step comprises hydrothermal refluxing.

8. A method as claimed in claim 1, wherein the at-least one metal sulfide comprises a mixture of two or more metal sulfides.

9. A method as claimed in claim 1, wherein the water-soluble sulfide is employed in an amount of about 0.1 to about 10 times the stoichiometric amount of the water-soluble sulfide required to react with the metal salt.

10. A method as claimed in claim 1, wherein the at least one metal salt is selected from the group consisting of: $Cd(NO_3)_2$, $Cd(ClO_4)_2$, $CdCl_2$, $CdSO_4$, cadmium acetate, $Zn(NO_3)_2$, $Zn(ClO_4)_2$, $ZnSO_4$, $ZnCl_2$, zinc acetate, $Mn(NO_3)_2$, $Mn(ClO_4)_2$, $MnSO_4$, $MnCl_2$, manganese acetate, $Pb(NO_3)_2$, $Pb(ClO_4)_2$, $PbSO_4$, $PbCl_2$, and lead acetate.

11. A method as claimed in claim 1, wherein the molar ratio of thiol groups to metal is from about 1 to about 100.

12. A method as claimed in claim 1, wherein the molar ratio of thiol groups to metal is from about 1 to about 5.

13. A method as claimed in claim 1, wherein the metal salt is cadmium nitrate, the thiol-containing molecule is 3-mercaptopropionic acid and the sulfide is sodium sulfide.

14. A method as claimed in claim 1, wherein the process is performed in an atmosphere that is substantially free of oxygen.

15. A method as claimed in claim 2, wherein the metal salt is zinc nitrate, the thiol-containing molecule is 3-mercaptopropionic acid and the sulfide is sodium sulfide.

* * * * *

UNITED STATES PATENT AND TRADEMARK OFFICE
CERTIFICATE OF CORRECTION

PATENT NO. : 7,335,345 B2  Page 1 of 1
APPLICATION NO. : 11/136653
DATED : February 26, 2008
INVENTOR(S) : Wei-Heng Shih et al.

It is certified that error appears in the above-identified patent and that said Letters Patent is hereby corrected as shown below:

In the Statement of Government Interest, column 1, line 15 change "RO1 EB00720-01" to --RO1 EB000720-02--

Signed and Sealed this

Sixteenth Day of March, 2010

David J. Kappos
*Director of the United States Patent and Trademark Office*